(12) United States Patent  
Sakuma et al.

(10) Patent No.: US 9,034,301 B2  
(45) Date of Patent: May 19, 2015

(54) REMINERALIZATION PROMOTER AND COMPOSITION FOR ORAL CAVITY

(75) Inventors: Shuji Sakuma, Tokyo (JP); Tsutomu Ishizaki, Tokyo (JP); Tadayoshi Arakawa, Tokyo (JP)

(73) Assignee: KABUSHIKI KAISHA SANGI, Tokyo (JP)

( * ) Notice: Subject to any disclaimer, the term of this patent is extended or adjusted under 35 U.S.C. 154(b) by 545 days.

(21) Appl. No.: 12/594,230

(22) PCT Filed: Apr. 8, 2008

(86) PCT No.: PCT/JP2008/000909  
§ 371 (c)(1), (2), (4) Date: Oct. 1, 2009

(87) PCT Pub. No.: WO2008/126410  
PCT Pub. Date: Oct. 23, 2008

(65) Prior Publication Data  
US 2010/0129298 A1 May 27, 2010

(30) Foreign Application Priority Data  
Apr. 10, 2007 (JP) .................................. 2007-103135

(51) Int. Cl.  
*A61Q 11/00* (2006.01)  
*A61K 8/24* (2006.01)  
(Continued)

(52) U.S. Cl.  
CPC ... *A61K 8/24* (2013.01); *A61K 8/55* (2013.01); *A61K 33/24* (2013.01); *A61Q 11/00* (2013.01); *C01B 25/322* (2013.01)

(58) Field of Classification Search  
CPC ......... A61Q 11/00; A61K 8/24; A61K 33/24; A61K 8/55

USPC .............................................. 424/49, 57, 602  
See application file for complete search history.

(56) References Cited

U.S. PATENT DOCUMENTS 5,037,639 A  8/1991  Tung  
5,268,167 A * 12/1993  Tung ................................ 424/52  
(Continued)

FOREIGN PATENT DOCUMENTS

CN  1330534  1/2002  
JP  9-20508  1/1997  
(Continued)

OTHER PUBLICATIONS

M Uota, H Arakawa, N Kitamura, T Yoshimura, J Tanaka, T Kijima. "Synthesis of High Surface Area Hydroxyapatite Nanoparticles by Mixed Surfactant-Mediated Approach." Langmuir, vol. 21, 2005, pp. 4724-4728 and pp. 1-4 of suppelenary information.*  
(Continued)

*Primary Examiner* — Frederick Krass  
*Assistant Examiner* — Tracy Liu  
(74) *Attorney, Agent, or Firm* — Kenneth H. Sonnenfeld; Margaret B. Brivanlou; King & Spalding LLP

(57) ABSTRACT

It is intended to provide a remineralization promoter for tooth enamel and a composition for an oral cavity, which can highly effectively promote the remineralization of tooth enamel and strongly inhibit dental caries. The remineralization promoter for tooth enamel and the composition for an oral cavity are characterized by containing amorphous hydroxyapatite and/or amorphized hydroxyapatite showing two peaks at $2\theta=31$ to $35°$ in X-ray diffraction. The amorphized hydroxyapatite is obtained by reacting calcium salt with phosphate in an aqueous solution and drying the reaction solution at a temperature of 10 to 70° C.

2 Claims, 3 Drawing Sheets

(51) Int. Cl.
*A61K 33/42* (2006.01)
*A61K 8/55* (2006.01)
*A61K 33/24* (2006.01)
*C01B 25/32* (2006.01)

(56) References Cited

U.S. PATENT DOCUMENTS

2008/0171001 A1* 7/2008 Engelman et al. .............. 424/50
2010/0143271 A1* 6/2010 Yang et al. ...................... 424/52

FOREIGN PATENT DOCUMENTS

| | | |
|---|---|---|
| JP | 09-202717 | 8/1997 |
| JP | 2001-122748 | 5/2001 |
| JP | 2003-34629 | 2/2003 |
| JP | 2004-35416 | 2/2004 |

OTHER PUBLICATIONS

Office Action issued in corresponding Chinese Patent Application No. 200880007610.7 dated Mar. 28, 2011.

* cited by examiner

REMINERALIZATION PROMOTER AND COMPOSITION FOR ORAL CAVITY

TECHNICAL FIELD

The present invention relates to a remineralization promoter for tooth enamel and a composition for an oral cavity.

BACKGROUND ART

Dental caries starts with plaque formation by cariogenic bacteria of tooth decay adhering to tooth surface. The cariogenic bacteria of tooth decay in the plaques metabolize foods to produce acids. These acids decalcify the tooth enamel by dissolving calcium or phosphorus immediately below the tooth surface, resulting in an incipient enamel caries state. Saliva has the function of remineralizing this demineralized part by the action of calcium or phosphorus contained therein and restoring the tooth. Moreover, a dentifrice for promoting remineralization has been produced, which is formulated with microparticles of a fluoride or of hydroxyapatite which is a calcium phosphate having a crystal structure similar to that of tooth minerals.

However, only the use of saliva or a fluoride or hydroxyapatite dentifrice is insufficient for remineralizing the demineralized part. Moreover, a chewing gum or the like for promoting remineralization has been produced, which is formulated with xylitol and calcium phosphate, or phosphoryl oligosaccharides of calcium. However, the chewing gum or the like formulated with xylitol or various calcium phosphates is insufficient for remineralizing the demineralized part.

Thus, studies have been made to enhance the effect of hydroxyapatite on dental caries, and preparations have been proposed, such as: a dentifrice for an oral cavity which is formulated with hydroxyapatite of 0.05 μm to 1.0 μm in particle size and can enhance repair of minute roughness in tooth surface, tooth surface protection, tooth decay prevention, dentin reinforcement, and whitening effect (see Patent Document 1); a composition for an oral cavity which is formulated with low crystalline hydroxyapatite and can prevent oral diseases or discomfort by adsorbing onto oral bacteria for their eradication (see Patent Document 2); and a 3DS home care agent for eradication of cariogenic bacteria of tooth decay, which is formulated with low crystalline or amorphous hydroxyapatite (see Patent Document 3).

Patent Document 1: Japanese Patent Laid-Open No. 9-202717
Patent Document 2: Japanese Patent Laid-Open No. 2001-122748
Patent Document 3: Japanese Patent Laid-Open No. 2004-35416

DISCLOSURE OF THE INVENTION

Problems to be Solved by the Invention

Hydroxyapatite is generally known to promote the remineralization of tooth enamel. This fact is also described in Patent Documents 1 to 3 described above. However, it was unknown that hydroxyapatites significantly differ in their effects of remineralizing tooth enamel, depending on the degree of crystallinity.

An object of the present invention is to provide a remineralization promoter for tooth enamel and a composition for an oral cavity, which can highly effectively promote the remineralization of tooth enamel and strongly inhibit dental caries.

Means for Solving the Problems

Low crystalline hydroxyapatite is known to be obtained by reacting calcium salt with phosphate in an aqueous solution and drying the reaction solution at a low temperature of 100° C. or lower. No study has been made on the difference of functions among a group of hydroxyapatites called low crystalline hydroxyapatites, and it has been thought that their functions do not largely differ. In actual practice, the drying has been performed at 100° C. in terms of drying time (production efficiency).

However, the present inventors produced hydroxyapatite (amorphized hydroxyapatite) by drying at a temperature lower than 100° C. (e.g., room temperature to 70° C.) without being constrained by production efficiency, and examined its function. As a result, the present inventors completed the present invention by finding that, unexpectedly, the amorphized hydroxyapatite can dramatically promote the remineralization of tooth enamel, compared with highly crystalline hydroxyapatite or low crystalline hydroxyapatite obtained by drying at 100° C.

Specifically, the present invention relates to: (1) a remineralization promoter for tooth enamel characterized by containing amorphous hydroxyapatite and/or amorphized hydroxyapatite; (2) the remineralization promoter for tooth enamel according to (1), wherein the amorphized hydroxyapatite is hydroxyapatite showing two peaks at $2\theta=31$ to $35°$ in X-ray diffraction; (3) the remineralization promoter for tooth enamel according to (2), wherein the amorphized hydroxyapatite is hydroxyapatite showing an X-ray diffraction pattern shown in FIG. 2; and (4) the remineralization promoter for tooth enamel according to any one of (1) to (3), wherein the amorphized hydroxyapatite is hydroxyapatite obtained by reacting calcium salt with phosphate in an aqueous solution and drying the reaction solution at a temperature of 10 to 70° C.

Moreover, the present invention relates to: (5) a composition for an oral cavity characterized by containing amorphous hydroxyapatite and/or amorphized hydroxyapatite; (6) the composition for an oral cavity according to (5), wherein the amorphized hydroxyapatite is hydroxyapatite showing two peaks at $2\theta=31$ to $35°$ in X-ray diffraction; (7) the composition for an oral cavity according to (6), wherein the amorphized hydroxyapatite is hydroxyapatite showing an X-ray diffraction pattern shown in FIG. 2; (8) the composition for an oral cavity according to any one of (5) to (7), wherein the amorphized hydroxyapatite is hydroxyapatite obtained by reacting calcium salt with phosphate in an aqueous solution and drying the reaction solution at a temperature of 10 to 70° C.; (9) the composition for an oral cavity according to any one of (5) to (8), wherein the content of the amorphous hydroxyapatite and/or the amorphized hydroxyapatite is 0.01 to 50% by weight; and (10) the composition for an oral cavity according to any one of (5) to (9), wherein the composition for an oral cavity is a dentifrice, mouth wash, or chewing gum.

Effects of the Invention

The remineralization promoter for tooth enamel and the composition for an oral cavity of the present invention can highly effectively promote the remineralization of tooth enamel and strongly inhibit dental caries.

BEST MODE OF CARRYING OUT THE INVENTION

A remineralization promoter for tooth enamel and a composition for an oral cavity of the present invention are not particularly limited as long as they contain amorphous hydroxyapatite and/or amorphized hydroxyapatite. The remineralization promoter for tooth enamel and the composition for an oral cavity of the present invention can promote the remineralization of tooth enamel more effectively and efficiently than those containing highly crystalline hydroxyapatite or low crystalline hydroxyapatite obtained by drying at 100° C.

Hydroxyapatite is usually represented by the stoichiometric composition $Ca_{10}(PO_4)_6(OH)_2$. Even non-stoichiometric hydroxyapatite, which has a Ca/P molar ratio less than 1.67, is characterized in that it can show hydroxyapatite properties and assume an apatite structure. The Ca/P molar ratio of hydroxyapatite is controlled by controlling the mixing ratio of salts as raw materials and synthesis conditions. For example, in the wet synthesis method of hydroxyapatite, the Ca/P molar ratio can be increased by adjusting an aqueous solution to basicity with ammonia water or the like during synthesis and decreased by adjusting an aqueous solution to neutral or weak acidity with dilute acid during synthesis. In the remineralization promoter for tooth enamel and the composition for an oral cavity of the present invention, both the hydroxyapatites having stoichiometric and non-stoichiometric compositions can be used, and those having a Ca/P molar ratio of 1.56 to 1.68 can be used.

Figure 1:
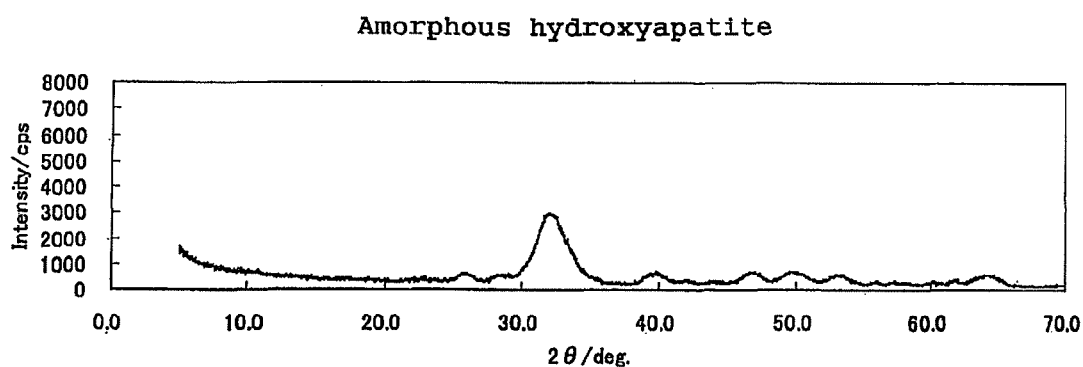
FIG. 1 It is a diagram showing an X-ray diffraction pattern of amorphous hydroxyapatite powder (dried at 60° C.) according to the present invention.
Figure 2:
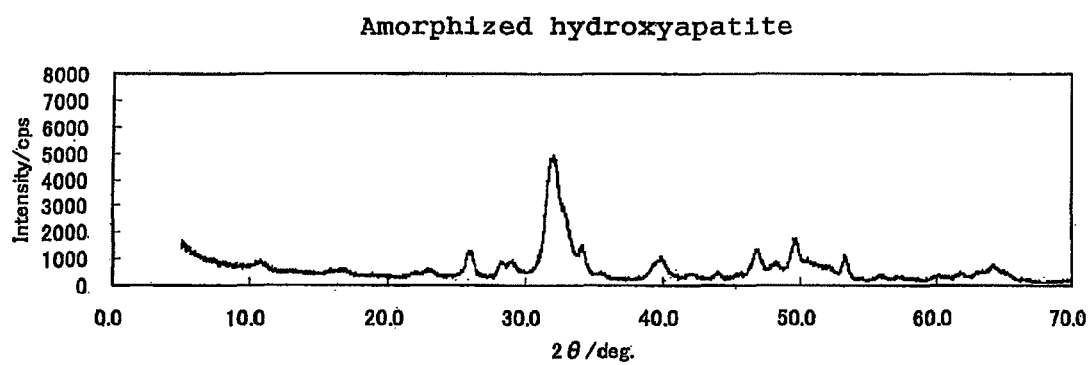
FIG. 2 It is a diagram showing an X-ray diffraction pattern of amorphized hydroxyapatite powder (freeze-dried) according to the present invention.
Figure 3:
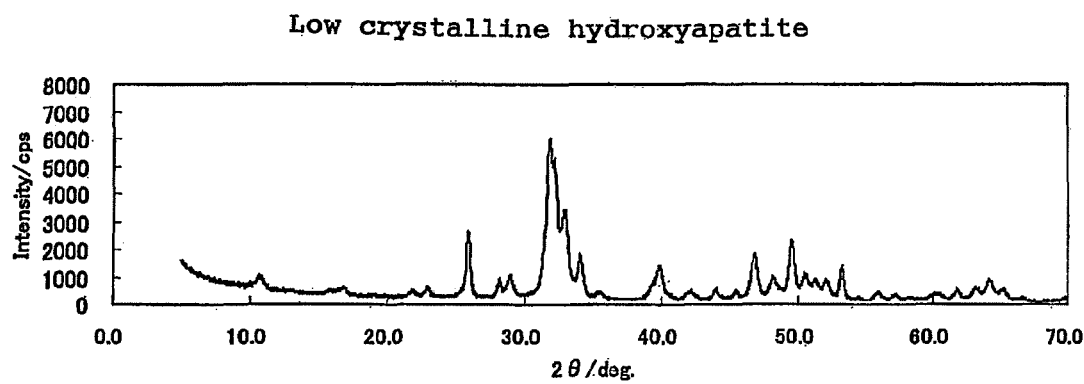
FIG. 3 It is a diagram showing an X-ray diffraction pattern of low crystalline hydroxyapatite powder (dried at 100° C.).
Figure 4:
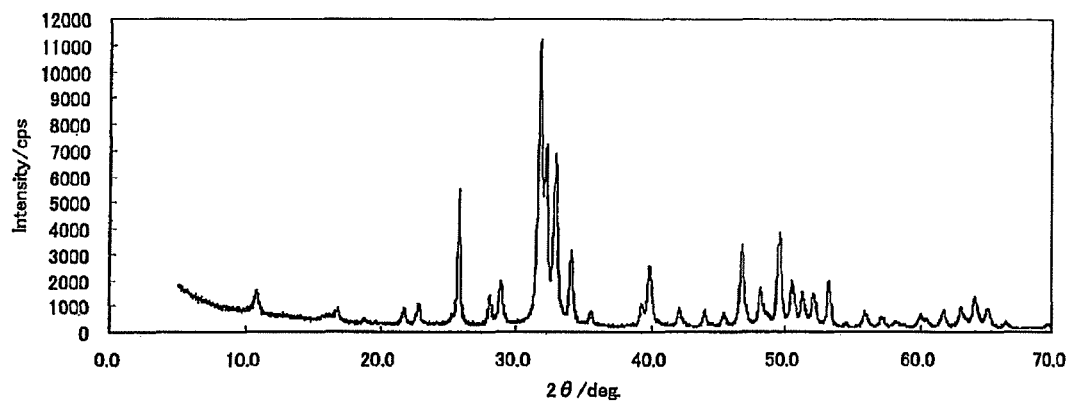
FIG. 4 It is a diagram showing an X-ray diffraction pattern of highly crystalline hydroxyapatite powder (sintered at 800° C.).

The X-ray diffraction pattern of amorphous hydroxyapatite powder (dried at 60° C.) according to the present invention is shown in FIG. 1. The X-ray diffraction pattern of amorphized hydroxyapatite powder (freeze-dried) according to the present invention is shown in FIG. 2. Moreover, for comparison, the X-ray diffraction pattern of low crystalline hydroxyapatite powder (dried at 100° C.) is shown in FIG. 3. The X-ray diffraction pattern of highly crystalline hydroxyapatite powder (sintered at 800° C.) is shown in FIG. 4. In this context, an X-ray diffraction apparatus (MXP18VAHF) (manufactured by MAC Science Co., Ltd.) was used in the measurement.

As shown in FIG. 4, the highly crystalline hydroxyapatite shows that four peaks at 2θ=31 to 35° are completely separate, demonstrating high crystallinity. As shown in FIG. 3, the low crystalline hydroxyapatite shows that, of these four peaks, two peaks around 2θ=31 to 33° overlap with each other and are not completely separate, demonstrating low crystallinity. In contrast to these X-ray diffraction patterns, as shown in FIG. 1, the amorphous hydroxyapatite according to the present invention shows that the peaks around 2θ=31 to 35° appear as one broad peak, demonstrating amorphism. Moreover, as shown in FIG. 2, the amorphized hydroxyapatite according to the present invention shows that three peaks around 2θ=31 to 34° overlap with each other, demonstrating almost amorphism (amorphized) although low crystallization starts to appear.

Specifically, the dried amorphous hydroxyapatite according to the present invention is hydroxyapatite showing one broad peak at 2θ=31 to 35° in X-ray diffraction. The dried amorphized hydroxyapatite according to the present invention is hydroxyapatite showing two peaks at 2θ=31 to 35° in X-ray diffraction.

Thus, the amorphous hydroxyapatite and the amorphized hydroxyapatite according to the present invention, unlike the crystalline hydroxyapatites, have an incomplete crystal structure, which shows weak diffraction in X-ray diffraction patterns. Moreover, the amorphous hydroxyapatite and the amorphized hydroxyapatite according to the present invention have a specific surface of approximately 60 $m^2/g$ in a BET method.

Methods for producing the amorphous hydroxyapatite and the amorphized hydroxyapatite according to the present invention are not particularly limited as long as the production methods can produce those showing the X-ray diffraction patterns as described above. The amorphous hydroxyapatite and the amorphized hydroxyapatite according to the present invention can be obtained, for example, by reacting calcium salt with phosphate in an aqueous solution and drying the reaction solution at the predetermined temperature. The reaction of calcium salt with phosphate can be performed, for example, by keeping a mixture solution of the calcium salt and the phosphate at room temperature for 2 to 3 days. Examples of the calcium salt can include general calcium salts such as calcium hydroxide, calcium acetate, calcium carbonate, calcium chloride, calcium citrate, and calcium lactate. Examples of the phosphate can include general phosphates such as phosphoric acid, ammonium phosphate, sodium phosphate, potassium phosphate, pyrophosphoric acid, and sodium hexametaphosphate.

For example, a suspension (reaction solution) within 1 week after preparation or this suspension that is freeze-dried can be used as the amorphous hydroxyapatite according to the present invention. The freeze drying is usually performed within 1 week, preferably 3 days, after the preparation of the suspension, although it differs depending on the production temperature or storage temperature of the solution.

Moreover, for example, a suspension (reaction solution) stored for a period exceeding 1 week after preparation or this prepared suspension that is dried at a temperature of 10 to 70° C., preferably 40 to 70° C., can be used as the amorphized hydroxyapatite according to the present invention. Alternatively, the prepared suspension may be dried after long-term storage at room temperature or lower. Thus, the amorphized hydroxyapatite according to the present invention is suitable to industrial use because of its easy production and storage.

Moreover, the amorphized hydroxyapatite can also be obtained by mechanically pulverizing low crystalline hydroxyapatite powder or low crystalline hydroxyapatite in a suspension form. For the mechanical pulverization, a bead mill, sand mill, high-speed impact mill, or high-pressure wet atomization apparatus can be used. Examples of the bead mill or sand mill can include VISCO MILL manufactured by IMEX CO., Ltd., GRAIN MILL manufactured by ASADA IRON WORKS CO., LTD., Dyno-mill manufactured by Shinmaru Enterprises Corp., Annular Mill manufactured by Mitsui Mining Co., Ltd., Sand Mill manufactured by INOUE MANUFACTURING CO., LTD., and Sand Mill manufactured by Kotobuki Engineering & Manufacturing Co., Ltd. Examples of the high-speed impact mill can include Ultra-High-Pressure Homogenizer manufactured by MIZUHO Industrial CO., LTD. Examples of the high-pressure wet atomization apparatus can include Nanomizer manufactured by Nanomizer Inc. and Atomization Apparatus manufactured by Sugino Machine Ltd. In this context, the hydroxyapatite after the wet pulverization can be dried at 10 to 70° C., preferably 40 to 70° C., and this powder shows the same X-ray diffraction pattern as that of FIG. 2.

The content of the amorphous hydroxyapatite and the amorphized hydroxyapatite in the remineralization promoter of the present invention is, for example, 50 to 100% by weight, preferably 75 to 100% by weight, more preferably 80 to 99% by weight, with respect to the total weight of formulation ingredients. Moreover, the content of the amorphous hydroxyapatite and the amorphized hydroxyapatite in the composition for an oral cavity of the present invention is, for example, 0.01 to 50% by weight, preferably 0.1 to 30% by weight, with respect to the total weight of the composition from the viewpoint of the effect of preventing dental caries, production cost, and usability.

The remineralization promoter and the composition for an oral cavity of the present invention may contain, in addition to the amorphous hydroxyapatite or the amorphized hydroxyapatite, additives used in usual compositions for an oral cavity (e.g., an abrasive, a humectant, a foaming agent, a thickener, a preservative, a flavor, and a sweetener) and various active ingredients, and so on. Specific examples of these components are shown below. In this context, the amounts of these arbitrary components formulated are appropriately selected within a pharmaceutically acceptable range that does not hinder the advantages of the present invention.

Abrasive: calcium carbonate, calcium hydrogen phosphate, calcium pyrophosphate, tricalcium phosphate, silica, aluminum silicate, aluminum hydroxide, alumina, zeolite, titanium oxide, zirconium silicate, etc.

Humectant: glycerin, propylene glycol, polyethylene glycol, sorbitol, xylitol, etc.

Foaming agent: sodium lauryl sulfate, N-lauroylsarcosine sodium, nonionic surfactants, etc.

Thickener: hydroxyethylcellulose, carboxymethylcellulose sodium, carrageenan, carboxyvinyl polymers, xanthan gum, gelatin, pullulan, sodium alginate, etc.

Preservative: p-hydroxybenzoic acid ester, alkyldiaminoethylglycine hydrochloride, methylparaben, ethylparaben, sodium benzoate, etc.

Flavor: menthol, spearmint oil, lemon oil, eucalyptus oil, etc.

Sweetener: saccharin sodium, stevia extracts, aspartame, etc.

Other active ingredients: allantoin, tocopherol acetate, isopropylphenol, β-glycyrrhetinic acid, triclosan, chlorhexidine, dextranase, chlorophyll, flavonoid, tranexamic acid, hinokitiol, etc.

Specific examples of the composition for an oral cavity of the present invention can include dentifrices (e.g., tooth pastes, tooth powders, and liquid dentifrices), mouth washes, and chewing gums.

In the production of the remineralization promoter and the composition for an oral cavity of the present invention, the amorphous hydroxyapatite, the amorphized hydroxyapatite, and other additives may be added in any course of the production process. Moreover, the composition for an oral cavity of the present invention can also be produced by formulating therein the remineralization promoter of the present invention.

Examples

Hereinafter, the present invention will be described with reference to Examples and Test Examples. However, Examples described below are used for describing a remineralization test, and the scope of the present invention is not intended to be limited to them.

(Preparation of Amorphous Hydroxyapatite)

A phosphate solution was added dropwise into a calcium hydroxide solution with stirring, and the mixture solution was kept at room temperature for 3 days. The suspension was freeze-dried to obtain amorphous hydroxyapatite. The obtained amorphous hydroxyapatite had a maximum particle size of approximately 0.8 μm, a minimum particle size of approximately 0.03 μm, and an average particle size of approximately 0.08 μm. In this context, the particle size was measured using Microtrac particle size distribution analyzer 7340UPA (manufactured by NIKKISO CO., LTD.). Moreover, it showed an X-ray diffraction pattern shown in FIG. 1.

(Preparation of Amorphized Hydroxyapatite)

A phosphate solution was added dropwise into a calcium hydroxide solution with stirring, and the mixture solution was kept at room temperature for 3 days. The suspension was blow-dried at 60° C. for 24 hours to obtain amorphized hydroxyapatite. The obtained amorphized hydroxyapatite had a maximum particle size of approximately 0.8 μm, a minimum particle size of approximately 0.03 μm, and an average particle size of approximately 0.08 μm. It showed an X-ray diffraction pattern shown in FIG. 2.

(Preparation of Low Crystalline Hydroxyapatite)

The suspension thus obtained was dried at 100° C. for 2 hours to obtain low crystalline hydroxyapatite. The obtained low crystalline hydroxyapatite had a maximum particle size of approximately 10 μm, a minimum particle size of approximately 0.05 μm, and an average particle size of approximately 1.2 μm. It showed an X-ray diffraction pattern shown in FIG. 3.

(Preparation of Highly Crystalline Hydroxyapatite)

A portion of the low crystalline hydroxyapatite thus obtained was sintered at 800° C. for 2 hours in air to obtain highly crystalline hydroxyapatite. The obtained highly crystalline hydroxyapatite had a maximum particle size of approximately 40 μm, a minimum particle size of approximately 0.1 μm, and an average particle size of approximately 3.7 μm. It showed an X-ray diffraction pattern shown in FIG. 4.

(Production of Compositions for an Oral Cavity of Examples and Comparative Examples)

Dentifrices, mouth washes, and chewing gums having the compositions shown below were produced according to standard methods. Among Examples, Examples 1 to 12 are dentifrices, Examples 13 to 20 are mouth washes, and Examples 21 to 30 are chewing gums. Of them, Examples 1 to 6, 13 to 16, and 21 to are examples using the amorphous hydroxyapatite, and Examples 7 to 12, 17 to 20, and 26 to 30 are examples using the amorphized hydroxyapatite. Moreover, among Comparative Examples, Comparative Examples 1 to 12 are dentifrices, Comparative Examples 13 to 20 are mouth washes, and Comparative Examples 21 to 30 are chewing gums. Of them, Comparative Examples 1 to 6, 13 to 16, and 21 to 25 are examples using the low crystalline hydroxyapatite, and Comparative Examples 7 to 12, 17 to 20, and 26 to 30 are examples using the highly crystalline hydroxyapatite.

TABLE 1

| | Dentifrice | | | | | |
|---|---|---|---|---|---|---|
| | Ex. 1 | Ex. 2 | Ex. 3 | Ex. 4 | Ex. 5 | Ex. 6 |
| Amorphous hydroxyapatite | 0.1 | 1.0 | 5.0 | 10.0 | 30.0 | 50.0 |
| Glycerin | 20.0 | 20.0 | 20.0 | 20.0 | 20.0 | 20.0 |
| Polyethylene glycol | 3.0 | 3.0 | 3.0 | 3.0 | 3.0 | 3.0 |
| Sodium lauryl sulfate | 1.0 | 1.0 | 1.0 | 1.0 | 1.0 | 1.0 |
| Xanthan gum | 0.5 | 0.5 | 0.5 | 0.5 | 0.5 | 0.5 |
| Hydroxyethylcellulose | 0.5 | 0.5 | 0.5 | 0.5 | 0.5 | 0.5 |
| Menthol | 0.5 | 0.5 | 0.5 | 0.5 | 0.5 | 0.5 |
| Purified water | Balance | Balance | Balance | Balance | Balance | Balance |
| Total | 100.0 | 100.0 | 100.0 | 100.0 | 100.0 | 100.0 |

TABLE 2

| | Dentifrice | | | | | |
|---|---|---|---|---|---|---|
| | Ex. 7 | Ex. 8 | Ex. 9 | Ex. 10 | Ex. 11 | Ex. 12 |
| Amorphized hydroxyapatite | 0.1 | 1.0 | 5.0 | 10.0 | 30.0 | 50.0 |
| Glycerin | 20.0 | 20.0 | 20.0 | 20.0 | 20.0 | 20.0 |
| Polyethylene glycol | 3.0 | 3.0 | 3.0 | 3.0 | 3.0 | 3.0 |
| Sodium lauryl sulfate | 1.0 | 1.0 | 1.0 | 1.0 | 1.0 | 1.0 |
| Xanthan gum | 0.5 | 0.5 | 0.5 | 0.5 | 0.5 | 0.5 |
| Hydroxyethylcellulose | 0.5 | 0.5 | 0.5 | 0.5 | 0.5 | 0.5 |
| Menthol | 0.5 | 0.5 | 0.5 | 0.5 | 0.5 | 0.5 |
| Purified water | Balance | Balance | Balance | Balance | Balance | Balance |
| Total | 100.0 | 100.0 | 100.0 | 100.0 | 100.0 | 100.0 |

TABLE 3

| | Dentifrice | | | | | |
|---|---|---|---|---|---|---|
| | Com. Ex. 1 | Com. Ex. 2 | Com. Ex. 3 | Com. Ex. 4 | Com. Ex. 5 | Com. Ex. 6 |
| Low crystalline hydroxyapatite | 0.1 | 1.0 | 5.0 | 10.0 | 30.0 | 50.0 |
| Glycerin | 20.0 | 20.0 | 20.0 | 20.0 | 20.0 | 20.0 |
| Polyethylene glycol | 3.0 | 3.0 | 3.0 | 3.0 | 3.0 | 3.0 |
| Sodium lauryl sulfate | 1.0 | 1.0 | 1.0 | 1.0 | 1.0 | 1.0 |
| Xanthan gum | 0.5 | 0.5 | 0.5 | 0.5 | 0.5 | 0.5 |
| Hydroxyethylcellulose | 0.5 | 0.5 | 0.5 | 0.5 | 0.5 | 0.5 |
| Menthol | 0.5 | 0.5 | 0.5 | 0.5 | 0.5 | 0.5 |
| Purified water | Balance | Balance | Balance | Balance | Balance | Balance |
| Total | 100.0 | 100.0 | 100.0 | 100.0 | 100.0 | 100.0 |

TABLE 4

| | Dentifrice | | | | | |
|---|---|---|---|---|---|---|
| | Com. Ex. 7 | Com. Ex. 8 | Com. Ex. 9 | Com. Ex. 10 | Com. Ex. 11 | Com. Ex. 12 |
| Highly crystalline hydroxyapatite | 0.1 | 1.0 | 5.0 | 10.0 | 30.0 | 50.0 |
| Glycerin | 20.0 | 20.0 | 20.0 | 20.0 | 20.0 | 20.0 |
| Polyethylene glycol | 3.0 | 3.0 | 3.0 | 3.0 | 3.0 | 3.0 |
| Sodium lauryl sulfate | 1.0 | 1.0 | 1.0 | 1.0 | 1.0 | 1.0 |
| Xanthan gum | 0.5 | 0.5 | 0.5 | 0.5 | 0.5 | 0.5 |

TABLE 4-continued

| | Dentifrice | | | | | |
|---|---|---|---|---|---|---|
| | Com. Ex. 7 | Com. Ex. 8 | Com. Ex. 9 | Com. Ex. 10 | Com. Ex. 11 | Com. Ex. 12 |
| Hydroxyethylcellulose | 0.5 | 0.5 | 0.5 | 0.5 | 0.5 | 0.5 |
| Menthol | 0.5 | 0.5 | 0.5 | 0.5 | 0.5 | 0.5 |
| Purified water | Balance | Balance | Balance | Balance | Balance | Balance |
| Total | 100.0 | 100.0 | 100.0 | 100.0 | 100.0 | 100.0 |

TABLE 5

| | Mouth wash | | | |
|---|---|---|---|---|
| | Ex. 13 | Ex. 14 | Ex. 15 | Ex. 16 |
| Amorphous hydroxyapatite | 0.001 | 0.01 | 0.1 | 2.0 |
| Ethyl alcohol | 10.0 | 10.0 | 10.0 | 10.0 |
| Sodium lauryl sulfate | 1.0 | 1.0 | 1.0 | 1.0 |
| Glycerin | 10.0 | 10.0 | 10.0 | 10.0 |
| Menthol | 0.4 | 0.4 | 0.4 | 0.4 |
| Purified water | Balance | Balance | Balance | Balance |
| Total | 100.0 | 100.0 | 100.0 | 100.0 |

TABLE 6

| | Mouth wash | | | |
|---|---|---|---|---|
| | Ex. 17 | Ex. 18 | Ex. 19 | Ex. 20 |
| Amorphized hydroxyapatite | 0.001 | 0.01 | 0.1 | 2.0 |
| Ethyl alcohol | 10.0 | 10.0 | 10.0 | 10.0 |
| Sodium lauryl sulfate | 1.0 | 1.0 | 1.0 | 1.0 |
| Glycerin | 10.0 | 10.0 | 10.0 | 10.0 |
| Menthol | 0.4 | 0.4 | 0.4 | 0.4 |
| Purified water | Balance | Balance | Balance | Balance |
| Total | 100.0 | 100.0 | 100.0 | 100.0 |

TABLE 7

| | Mouth wash | | | |
|---|---|---|---|---|
| | Com. Ex. 13 | Com. Ex. 14 | Com. Ex. 15 | Com. Ex. 16 |
| Low crystalline hydroxyapatite | 0.001 | 0.01 | 0.1 | 2.0 |
| Ethyl alcohol | 10.0 | 10.0 | 10.0 | 10.0 |
| Sodium lauryl sulfate | 1.0 | 1.0 | 1.0 | 1.0 |
| Glycerin | 10.0 | 10.0 | 10.0 | 10.0 |
| Menthol | 0.4 | 0.4 | 0.4 | 0.4 |
| Purified water | Balance | Balance | Balance | Balance |
| Total | 100.0 | 100.0 | 100.0 | 100.0 |

TABLE 8

| | Mouth wash | | | |
|---|---|---|---|---|
| | Com. Ex. 17 | Com. Ex. 18 | Com. Ex. 19 | Com. Ex. 20 |
| High crystalline hydroxyapatite | 0.001 | 0.01 | 0.1 | 2.0 |
| Ethyl alcohol | 10.0 | 10.0 | 10.0 | 10.0 |
| Sodium lauryl sulfate | 1.0 | 1.0 | 1.0 | 1.0 |
| Glycerin | 10.0 | 10.0 | 10.0 | 10.0 |

TABLE 8-continued

| | Mouth wash | | | |
|---|---|---|---|---|
| | Com. Ex. 17 | Com. Ex. 18 | Com. Ex. 19 | Com. Ex. 20 |
| Menthol | 0.4 | 0.4 | 0.4 | 0.4 |
| Purified water | Balance | Balance | Balance | Balance |
| Total | 100.0 | 100.0 | 100.0 | 100.0 |

TABLE 9

| | Chewing gum | | | | |
|---|---|---|---|---|---|
| | Ex. 21 | Ex. 22 | Ex. 23 | Ex. 24 | Ex. 25 |
| Amorphous hydroxyapatite | 0.1 | 1.0 | 5.0 | 10.0 | 20.0 |
| Gum base | 28.0 | 28.0 | 28.0 | 28.0 | 28.0 |
| Xylitol | 30.0 | 30.0 | 30.0 | 25.0 | 25.0 |
| Palatinit | 21.0 | 21.0 | 21.0 | 10.0 | 10.0 |
| Maltitol | 3.8 | 3.8 | 3.8 | 3.8 | 3.8 |
| Softener | 0.8 | 0.8 | 0.8 | 0.8 | 0.8 |
| Flavor | 1.0 | 1.0 | 1.0 | 1.0 | 1.0 |
| Reducing maltose syrup | Balance | Balance | Balance | Balance | Balance |
| Total | 100.0 | 100.0 | 100.0 | 100.0 | 100.0 |

TABLE 10

| | Chewing gum | | | | |
|---|---|---|---|---|---|
| | Ex. 26 | Ex. 27 | Ex. 28 | Ex. 29 | Ex. 30 |
| Amorphized hydroxyapatite | 0.1 | 1.0 | 5.0 | 10.0 | 20.0 |
| Gum base | 28.0 | 28.0 | 28.0 | 28.0 | 28.0 |
| Xylitol | 30.0 | 30.0 | 30.0 | 25.0 | 25.0 |
| Palatinit | 21.0 | 21.0 | 21.0 | 10.0 | 10.0 |
| Maltitol | 3.8 | 3.8 | 3.8 | 3.8 | 3.8 |
| Softener | 0.8 | 0.8 | 0.8 | 0.8 | 0.8 |
| Flavor | 1.0 | 1.0 | 1.0 | 1.0 | 1.0 |
| Reducing maltose syrup | Balance | Balance | Balance | Balance | Balance |
| Total | 100.0 | 100.0 | 100.0 | 100.0 | 100.0 |

TABLE 11

Chewing gum

|  | Com. Ex. 21 | Com. Ex. 22 | Com. Ex. 23 | Com. Ex. 24 | Com. Ex. 25 |
|---|---|---|---|---|---|
| Low crystalline hydroxyapatite | 0.1 | 1.0 | 5.0 | 10.0 | 20.0 |
| Gum base | 28.0 | 28.0 | 28.0 | 28.0 | 28.0 |
| Xylitol | 30.0 | 30.0 | 30.0 | 25.0 | 25.0 |
| Palatinit | 21.0 | 21.0 | 21.0 | 10.0 | 10.0 |
| Maltitol | 3.8 | 3.8 | 3.8 | 3.8 | 3.8 |
| Softener | 0.8 | 0.8 | 0.8 | 0.8 | 0.8 |
| Flavor | 1.0 | 1.0 | 1.0 | 1.0 | 1.0 |
| Reducing maltose syrup | Balance | Balance | Balance | Balance | Balance |
| Total | 100.0 | 100.0 | 100.0 | 100.0 | 100.0 |

TABLE 12

Chewing gum

|  | Com. Ex. 26 | Com. Ex. 27 | Com. Ex. 28 | Com. Ex. 29 | Com. Ex. 30 |
|---|---|---|---|---|---|
| High crystalline hydroxyapatite | 0.1 | 1.0 | 5.0 | 10.0 | 20.0 |
| Gum base | 28.0 | 28.0 | 28.0 | 28.0 | 28.0 |
| Xylitol | 30.0 | 30.0 | 30.0 | 25.0 | 25.0 |
| Palatinit | 21.0 | 21.0 | 21.0 | 10.0 | 10.0 |
| Maltitol | 3.8 | 3.8 | 3.8 | 3.8 | 3.8 |
| Softener | 0.8 | 0.8 | 0.8 | 0.8 | 0.8 |
| Flavor | 1.0 | 1.0 | 1.0 | 1.0 | 1.0 |
| Reducing maltose syrup | Balance | Balance | Balance | Balance | Balance |
| Total | 100.0 | 100.0 | 100.0 | 100.0 | 100.0 |

[Remineralization Promotion Test]

Artificial incipient enamel caries test samples prepared in advance were used to confirm the effect of promoting remineralization. The preparation of the artificial incipient enamel caries test samples was performed using the crown parts of human extracted teeth undergoing no conservative dentistry and prosthodontic treatment. Stains or deposits on the enamel surface were removed, and windows of 3.5×3.0 mm were then prepared in the site to be tested of the enamel surface using a nail enamel and dipped in a 0.1 M lactate buffer solution (pH 4.5, 3.0 mM $CaCl_2$, 1.8 mM $KH_2PO_4$, 0.5% CMC) at 37° C. for 7 days to prepare artificial incipient enamel caries. Among the windows of 3.5×3.0 mm, half the portion on the cusp side of the crown was further masked using a nail enamel and used as a site to be compared (control). Substances to be tested were prepared as follows: the dentifrice or the mouth wash was prepared into a suspension with artificial saliva, which was then used as a test solution; and the chewing gum was pulverized, and a water-soluble component was then extracted from each test substance and prepared into a suspension with artificial saliva, which was then used as a test solution.

Figure 5:
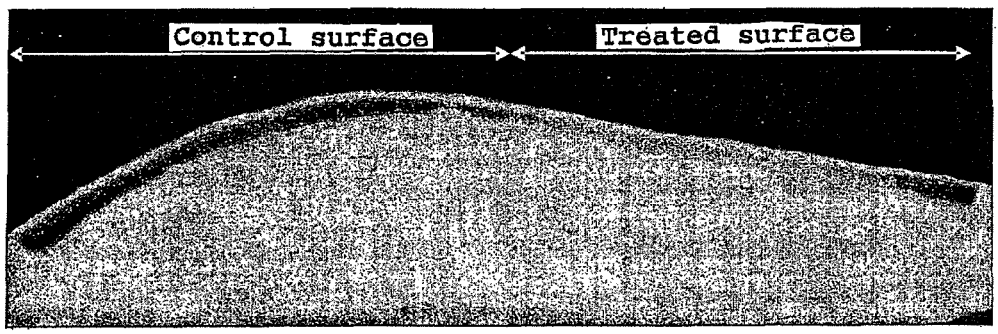
FIG. 5 It is a contact microradiography (CMR) photograph showing control and treated surfaces of a crown part.
Figure 6:
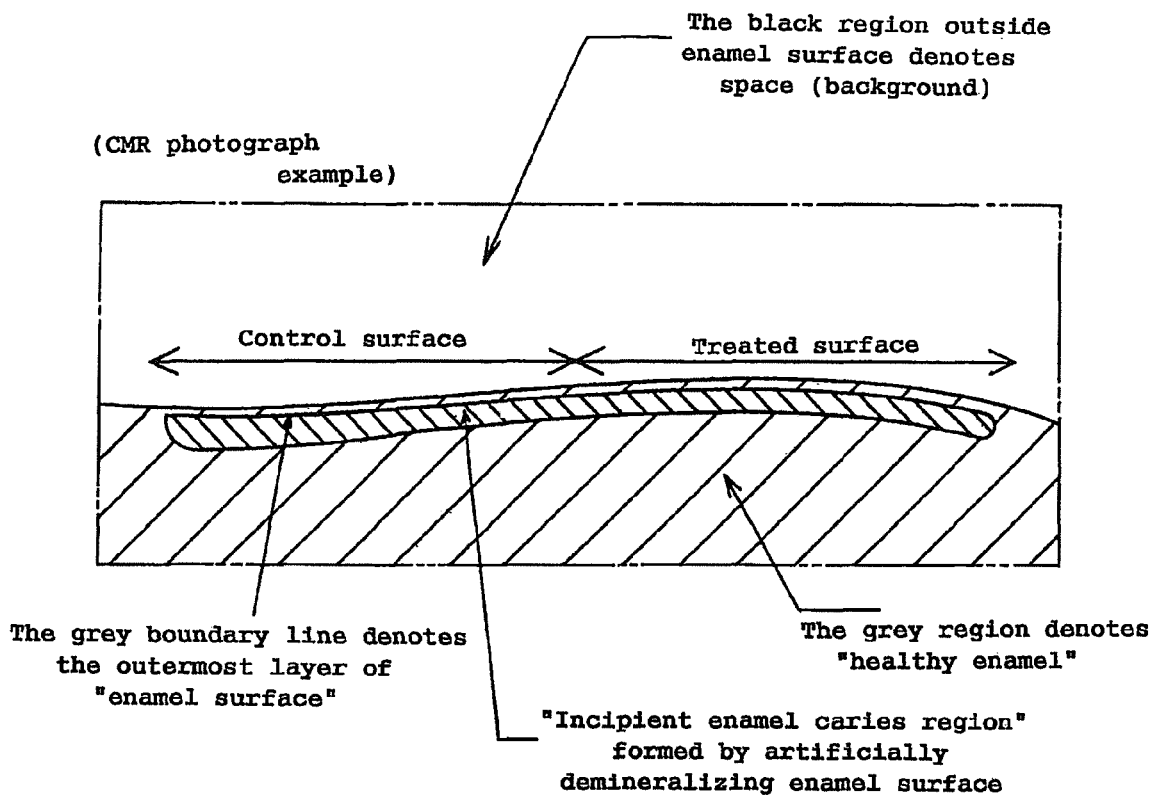
FIG. 6 It is a diagram illustrating the photograph shown in FIG. 5.

For the remineralization promotion test, the artificial incipient enamel caries test sample thus prepared was dipped in each test solution for 24 hours and then cut in parallel with the tooth axis into slices of approximately 500 μm in thickness using a micro-cutter. Then, the slices were polished with water poured using a synthetic or natural whetstone to obtain thin slices of approximately 100 μm in thickness parallel thereto. After the polishing, contact microradiography (CMR) was performed (see FIGS. 5 and 6) for confirming the effect of remineralizing the tooth. The effect of remineralizing the artificial incipient enamel caries site was analyzed using a computer.

In the image analysis using the computer, the amount of remineralized minerals was calculated based on the formula of Angmer et al. (B. Angmer, D. Carlstrom and J. E. Glas: Studies on Ultrastructure of Dental Enemel IV: The Mineralization of normal Human Enamel, J. Ultrastructure. Res. 8, 12-23, 1963), and the amounts of minerals lost ΔZ (% volume mineral/μm) from the control and treated surfaces of each slice were calculated according to the method of Damato et al. (F. A. Damato, R. Stang and K. W. Stephen: Effect of Fluoride Concentration on Remineralization of Carious Enamel: an in vitro pH-Cycling Study, Caries Res, 24, 174-180, 1990). In this context, the remineralization rate was calculated according to the following formula:

$$\text{Recalcification rate} = \frac{\Delta Z \text{ of control surface} - \Delta Z \text{ of treated surface}}{\Delta Z \text{ of control surface}} \times 100(\%) \quad \text{[Formula 1]}$$

Table 13 shows the results of confirming the effect of promoting remineralization by each composition for an oral cavity in the remineralization promotion test.

TABLE 13

| | Example | Ex. 1 | Ex. 2 | Ex. 3 | Ex. 4 | Ex. 5 | Ex. 6 |
|---|---|---|---|---|---|---|---|
| Dentifrice | Remineralization rate (%) | 18.1 | 25.4 | 32.7 | 37.1 | 39.5 | 40.8 |
| | Example | Ex. 7 | Ex. 8 | Ex. 9 | Ex. 10 | Ex. 11 | Ex. 12 |
| Dentifrice | Remineralization rate (%) | 17.9 | 25.3 | 32.2 | 36.7 | 39.0 | 40.4 |

| | | Example | | | | | |
|---|---|---|---|---|---|---|---|
| | | Com. Ex. 1 | Com. Ex. 2 | Com. Ex. 3 | Com. Ex. 4 | Com. Ex. 5 | Com. Ex. 6 |
| Dentifrice | Remineralization rate (%) | 8.2 | 9.1 | 10.6 | 11.3 | 13.7 | 19.2 |
| | | Com. Ex. 7 | Com. Ex. 8 | Com. Ex. 9 | Com. Ex. 10 | Com. Ex. 11 | Com. Ex. 12 |
| Dentifrice | Remineralization rate (%) | 2.1 | 7.6 | 8.3 | 9.9 | 12.5 | 15.6 |

| | Example | Ex. 13 | Ex. 14 | Ex. 15 | Ex. 16 |
|---|---|---|---|---|---|
| Mouth wash | Remineralization rate (%) | 2.7 | 4.9 | 7.6 | 9.0 |
| | Example | Ex. 17 | Ex. 18 | Ex. 19 | Ex. 20 |
| Mouth wash | Remineralization rate (%) | 2.7 | 4.4 | 7.2 | 8.8 |

| | | Example | | | |
|---|---|---|---|---|---|
| | | Com. Ex. 13 | Com. Ex. 14 | Com. Ex. 15 | Com. Ex. 16 |
| Mouth wash | Remineralization rate (%) | 1.2 | 1.5 | 2.8 | 3.5 |
| | | Com. Ex. 17 | Com. Ex. 18 | Com. Ex. 19 | Com. Ex. 20 |
| Mouth wash | Remineralization rate (%) | 1.0 | 1.1 | 1.6 | 1.8 |

| | Example | Ex. 21 | Ex. 22 | Ex. 23 | Ex. 24 | Ex. 25 |
|---|---|---|---|---|---|---|
| Chewing gum | Remineralization rate (%) | 4.2 | 6.8 | 8.5 | 19.6 | 30.0 |
| | Example | Ex. 26 | Ex. 27 | Ex. 28 | Ex. 29 | Ex. 30 |
| Chewing gum | Remineralization rate (%) | 4.0 | 6.8 | 8.1 | 19.6 | 29.4 |

| | | Example | | | | |
|---|---|---|---|---|---|---|
| | | Com. Ex. 21 | Com. Ex. 22 | Com. Ex. 23 | Com. Ex. 24 | Com. Ex. 25 |
| Chewing gum | Remineralization rate (%) | 1.1 | 2.9 | 3.8 | 5.6 | 6.3 |
| | | Com. Ex. 26 | Com. Ex. 27 | Com. Ex. 28 | Com. Ex. 29 | Com. Ex. 30 |
| Chewing gum | Remineralization rate (%) | 0.8 | 1.3 | 1.9 | 2.2 | 2.7 |

As shown in Table 13, the compositions for an oral cavity formulated with the amorphous hydroxyapatite or the amorphized hydroxyapatite according to Examples of the present invention have been demonstrated to have a dramatically improved tooth enamel remineralization rate, compared with the compositions for an oral cavity formulated with the highly crystalline hydroxyapatite or the low crystalline hydroxyapatite according to Comparative Examples. Specifically, in all the cases, the compositions for an oral cavity formulated with the amorphous hydroxyapatite or the amorphized hydroxyapatite according to Examples of the present invention exhibited a remineralization rate two times or more of that exhibited by the compositions for an oral cavity formulated with the low crystalline hydroxyapatite, and have thus been demonstrated to be highly excellent in the effect.

The invention claimed is:

1. A composition for an oral cavity comprising an amorphized hydroxyapatite,
    having an X-ray diffraction pattern as shown in FIG. 2,
    wherein said composition is selected from the group consisting of a dentifrice, mouthwash, and chewing gum.

2. The composition for an oral cavity according to claim 1, wherein the content of the amorphized hydroxyapatite is 0.01 to 50% by weight.

* * * * *